United States Patent
Ritz et al.

(10) Patent No.: US 10,633,395 B2
(45) Date of Patent: Apr. 28, 2020

(54) ARYLOXAZOLIDINONE ANTIBIOTIC COMPOUNDS

(71) Applicant: Idorsia Pharmaceuticals Ltd., Allschwil (CH)

(72) Inventors: Daniel Ritz, Allschwil (CH); Georg Rueedi, Allschwil (CH); Cornelia Zumbrunn, Allschwil (CH)

(73) Assignee: Idorsia Pharmaceuticals Ltd., Allschwil (CH)

( * ) Notice: Subject to any disclaimer, the term of this patent is extended or adjusted under 35 U.S.C. 154(b) by 0 days.

(21) Appl. No.: 16/486,794

(22) PCT Filed: Feb. 16, 2018

(86) PCT No.: PCT/EP2018/053873
§ 371 (c)(1),
(2) Date: Aug. 16, 2019

(87) PCT Pub. No.: WO2018/149960
PCT Pub. Date: Aug. 23, 2018

(65) Prior Publication Data
US 2019/0367532 A1    Dec. 5, 2019

(30) Foreign Application Priority Data
Feb. 17, 2017  (EP) .................................... 17156728

(51) Int. Cl.
C07D 498/04    (2006.01)
A61P 31/04    (2006.01)

(52) U.S. Cl.
CPC ............ C07D 498/04 (2013.01); *A61P 31/04* (2018.01)

(58) Field of Classification Search
None
See application file for complete search history.

(56) References Cited

U.S. PATENT DOCUMENTS 9,822,114 B2 * 11/2017 Hubschwerlen ..... C07D 471/06
2004/0152911 A1   8/2004 Bowman et al.

FOREIGN PATENT DOCUMENTS

| WO | 2007093963 A1 | 8/2007 |
|---|---|---|
| WO | 2008078305 A2 | 7/2008 |
| WO | 2008126024 A2 | 10/2008 |
| WO | 2008126034 A2 | 10/2008 |
| WO | 2008152603 A1 | 12/2008 |
| WO | 2009077989 A1 | 6/2009 |
| WO | 2009104147 A2 | 8/2009 |
| WO | 2009104159 A1 | 8/2009 |
| WO | 2009147616 A1 | 12/2009 |
| WO | 2010041194 A1 | 4/2010 |
| WO | 2010041218 A2 | 4/2010 |
| WO | 2010067332 A1 | 6/2010 |
| WO | 2010116337 A1 | 10/2010 |
| WO | 2013068948 A1 | 5/2013 |
| WO | 2014108832 A1 | 7/2014 |
| WO | 2014170821 A1 | 10/2014 |
| WO | 2014178008 A1 | 11/2014 |
| WO | 2016059097 A1 | 4/2016 |
| WO | 2017179002 A1 | 10/2017 |

OTHER PUBLICATIONS

International Search Report and Written Opinion corresponding to International Application No. PCT/EP2018/053873, dated Mar. 14, 2018.
Solomon, Steven L., et al., "Antibiotic Resistance Threats in the United States: Stepping Back from the Brink", American Family Physician, vol. 89, No. 12, pp. 938-941, Jun. 15, 2014.
Remington, The Science and Practice of Pharmacy, 21st Edition (2005), Part 5, "Pharmaceutical Manufacturing", published by Lippincott Williams & Wilkins.
Stahl, P. Heinrich et al., "Handbook of Pharmaceutical Salts Properties, Selection and Use", International Union of Pure and Applied Chemistry, pp. 329-350 (2008).
Johan Wouters and Luc Quéré (Eds.), "Pharmaceutical Salts and Co-crystals", RSC Publishing (2012).
"Methods for Dilution Antimicrobial Susceptibility Tests for Bacteria that Grow Aerobically", Approved standard, 7th Ed., Clinical and Laboratory Standards Institute (CLSI) Document M7-A7, vol. 26, No. 2 (2006).
Diaz, D. et al., "Evaluation of an automated in vitro micronucleus assay in CHO-K1 cells", Elsevier, Mutation Research 630, pp. 1-13 (2007).
Obach, R. Scott, et al., "The Prediction of Human Pharmacokinetic Parameters from Preclinical and In Vitro Metabolism Data", The Journal of Pharmacology and Experimental Therapeutics, 1997, vol. 283, No. 1, pp. 46-58.
Obach, R. Scott, "Nonspecific Binding to Microsomes: Impact on Scale-Up of In Vitro Intrinsic Clearance to Hepatic Clearance As Assessed Through Examination of Warfarin, Imipramine, and Propranolol", Drug Metabolism and Disposition, 1997, vol. 25, No. 12, pp. 1359-1369.

* cited by examiner

*Primary Examiner* — Kamal A Saeed
(74) *Attorney, Agent, or Firm* — Arent Fox, LLP

(57) ABSTRACT

The invention relates to aryloxazolidinone compounds of formula I:

wherein Y represents hydrogen or certain chemical groups. These compounds are useful antimicrobial agents effective against a variety of pathogens including inter alia Gram-negative aerobic and anaerobic bacteria.

9 Claims, No Drawings

ARYLOXAZOLIDINONE ANTIBIOTIC COMPOUNDS

CROSS-REFERENCE TO RELATED APPLICATIONS

This application is a filing under 35 U.S.C. 371 of international application number PCT/EP2018/053873, filed Feb. 16, 2018, which claims priority to application Ser. No. 17/156,728.2 filed in the European Patent Office on Feb. 17, 2017, the entire disclosures of each of which are hereby incorporated by reference.

The present invention concerns novel aryloxazolidinone compounds, pharmaceutical compositions containing them and uses of these compounds in the manufacture of medicaments for the treatment of bacterial infections. These compounds are useful antimicrobial agents effective against a variety of human and veterinary pathogens including among others Gram-positive and Gram-negative aerobic and anaerobic bacteria and especially against resistant strains of *Pseudomonas aeruginosa* and Enterobacteriaceae such as *Klebsiella pneumoniae*.

The intensive use of antibiotics has lead to a drastic increase in microorganisms with genetically based resistance mechanisms. Modern medicine and socio-economic behaviour exacerbate the problem of resistance development by creating slow growth situations for pathogenic microbes, e.g. in artificial joints, and by supporting long-term host reservoirs, e.g. in immune-compromised patients.

In hospital settings, an increasing number of strains of *Staphylococcus aureus, Streptococcus pneumoniae, Enterococcus* spp., Enterobacteriaceae and *Pseudomonas aeruginosa*, major sources of infections, are becoming multidrug-resistant and therefore difficult if not impossible to treat:

- *S. aureus* is resistant to beta-lactams, quinolones and now even to vancomycin;
- *S. pneumoniae* is becoming resistant to penicillin or quinolone antibiotics and even to new macrolides;
- *Enteroccocci* are quinolone and vancomycin resistant and beta-lactam antibiotics are inefficacious against these strains;
- Enterobacteriacea are cephalosporin- and quinolone-resistant and carbapenems are losing their efficacy (e.g. carbapenem-resistant *Klebsiella pneumoniae*);
- *P. aeruginosa* is beta-lactam and quinolone resistant.

Furthermore, the incidence of multidrug-resistant Gram-negative strains such as Enterobacteriaceae and *Pseudomonas aeruginosa*, is steadily increasing and new emerging organisms like *Acinetobacter* spp. or *Clostridium difficile*, which have been selected during therapy with the currently used antibiotics, are becoming a real problem in hospital settings (S. L. Solomon et al., Antibiotic Resistance Threats In the United States: Stepping Back from the Brink, *Academy of Family Physician*, page 940 Volume 89, Number 12, Jun. 15, 2014). Therefore, there is a high medical need for new antibacterial agents which overcome these multidrug resistances in bacteria, especially *Pseudomonas aeruginosa* and Enterobacteriaceae such as *Klebsiella pneumoniae*.

We have described ceratin aryloxazolidinone compounds and their antimicrobial properties in WO 2010/041194 and WO 2014/108832.

The present invention provides novel aryloxazolidinone S,S-stereoisomers which have advantageous pharmacological properties.

Various embodiments of the present invention are difined hereafter:

1) The first embodiment relates to compounds of formula I

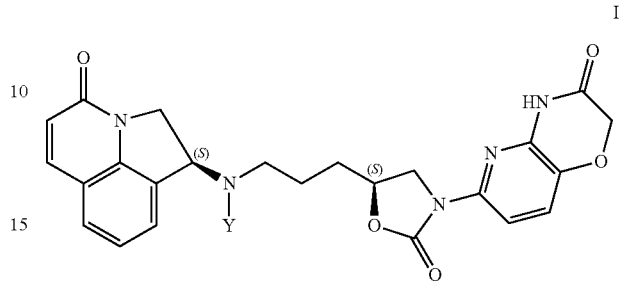

wherein Y represents hydrogen or a group selected from $Y^1$ and $Y^2$

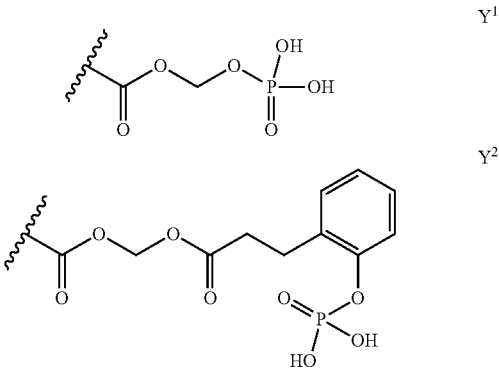

or a salt thereof.

2) Another embodiment relates to the compound of embodiment 1), wherein Y is hydrogen.
3) Another embodiment relates to the compound of embodiment 1), wherein Y is $Y^1$.
4) Another embodiment relates to the compound of embodiment 1), wherein Y is $Y^2$.

The compounds according to embodiments 3) and 4) exhibit antibacterial activity in biologically relevant environment (i.e. in the presence of a phosphatase, an esterase, a sulfatase or any suitable equivalent thereof capable of removing the group $Y^1$ or $Y^2$). In said enviorment said compounds are typically converted to the compound of embodiment 1).

The compounds according to any one of embodiments 1) to 4) are particularly active against bacteria and bacteria-like organisms. They may therefore be particularly suitable in human and veterinary medicine for the prophylaxis and chemotherapy of local and systemic infections caused by these pathogens as well as disorders related to bacterial infections comprising pneumonia, otitis media, sinusitis, bronchitis, tonsillitis, and mastoiditis related to infection by *Streptococcus pneumoniae, Moraxella catarrhalis, Staphylococcus aureus, Staphylococcus epidermidis, Staphylococcus haemolyticus,* or *Peptostreptococcus* spp.; pharyngitis, rheumatic fever, and glomerulonephritis related to infection by *Streptococcus pyogenes*, Groups C and G streptococci, *Corynebacterium diphtheriae,* or *Actinobacillus haemolyticum*; respiratory tract infections related to infection by

*Legionella pneumophila, S. pneumonia* or *Chlamydia pneumoniae*; blood and tissue infections, including endocarditis and osteomyelitis, caused by *S. aureus, S. haemolyticus*, including strains resistant to known antibacterials such as, but not limited to, beta-lactams, vancomycin, aminoglycosides, quinolones, chloramphenicol, tetracyclines and macrolides; uncomplicated skin and soft tissue infections and abscesses, and puerperal fever related to infection by *S. aureus*, coagulase-negative staphylococci (i.e., *S. epidermidis, S. haemolyticus*, etc.), *S. pyogenes, Streptococcus agalactiae*, Streptococcal groups C-F (minute colony streptococci), viridans streptococci, *Corynebacterium minutissimum, Clostridium* spp., or *Bartonella henselae*; uncomplicated acute urinary tract infections related to infection by *S. aureus* or coagulase-negative staphylococcal species; urethritis and cervicitis; sexually transmitted diseases related to infection by *Chlamydia trachomatis, Haemophilus ducreyi, Treponema pallidum, Ureaplasma urealyticum*, or *Neiserria gonorrheae*; toxin diseases related to infection by *S. aureus* (food poisoning and toxic shock syndrome), or Groups A, B and C streptococci; conjunctivitis, keratitis, and dacrocystitis related to infection by *C. trachomatis, N. gonorrhoeae, S. aureus, S. pneumoniae, S. pyogenes* or *Listeria* spp. The preceding lists of infections and pathogens are to be interpreted merely as examples and in no way as limiting.

The compounds according to one of embodiments 1) to 4) may be used for the preparation of a medicament, and are suitable, for the prevention or treatment of a bacterial infection selected from the group consisting of respiratory tract infections, otitis media, meningitis, skin and soft tissue infections (whether complicated or uncomplicated), pneumonia (including hospital acquired pneumonia), bacteremia, endocarditis, intraabdominal infections, gastrointestinal infections, urinary tract infections, sexually transmitted infections, foreign body infections, osteomyelitis, Lyme disease, topical infections, or ophthalmological infections, and notably for the prevention or treatment of a bacterial infection selected from the group consisting of respiratory tract infections, otitis media, meningitis, skin and soft tissue infections (whether complicated or uncomplicated), pneumonia (including hospital acquired pneumonia) and bacteremia.

The compounds according to one of embodiments 1) to 4) may further be useful for the preparation of a medicament, and are suitable, for the treatment of infections that are mediated by Gram positive bacteria (such as *Staphylococcus aureus, Bacillus cereus, Bacillus anthracis, Corynebacterium* spp. and *Propionibacterium acnes*), notably by Gram positive bacteria selected from the group consisting of *Bacillus cereus, Bacillus anthracis* and *Propionibacterium acnes*. In particular, The compounds according to one of embodiments 1) to 4) can be used for the preparation of a medicament, and are suitable, for the treatment of a bacterial infection mediated by *Staphylococcus aureus* (especially quinolone-resistant *Staphylococcus aureus* bacteria).

The compounds according to one of embodiments 1) to 4) may further be useful for the preparation of a medicament, and are suitable, for the treatment of infections that are mediated by Gram negative bacteria (such as *E. coli, Klebsiella pneumoniae* and other Enterobacteriaceae, *Pseudomonas aeruginosa, Stenotrophomonas maltophilia, Neisseria meningitidis, Moraxella catarrhalis* and *Bacteroides* spp), notably by Gram negative bacteria selected from the group consisting of *Escherichia coli, Klebsiella pneumoniae, Pseudomonas aeruginosa, Stenotrophomonas maltophilia, Moraxella catarrhalis* and *Neisseria meningitidis*. In particular, the compounds of formula I according to any one of embodiments 1) to 4), and the pharmaceutically acceptable salts thereof, can be used for the preparation of a medicament, and are suitable, for the treatment of a bacterial infection mediated by *Klebsiella pneumoniae* bacteria (especially multidrug-resistant or quinolone-resistant *Klebsiella pneumoniae* bacteria) and *Pseudomonas aeruginosa*.

One aspect of this invention therefore relates to the use of the compounds according to one of embodiments 1) to 4) for the manufacture of a medicament for the prevention or treatment of a bacterial infection (in particular one of the previously mentioned infections mediated by Gram negative bacteria or one of the previously mentioned infections mediated by Gram positive bacteria).

Another aspect of this invention relates to the use of at least one of the compounds according to embodiments 1) to 4) as a medicament.

Yet a further aspect of this invention relates to a composition comprising at least one of the compounds according to embodiments 1) to 4) and further at least one therapeutically inert excipient.

A pharmaceutical composition according to the present invention contains at least one of the compounds according to embodiments 1) to 4) as active agent and optionally carriers and/or diluents and/or adjuvants, and may also contain additional known antibiotics.

The production of the pharmaceutical compositions can be effected in a manner which will be familiar to any person skilled in the art (see for example Remington, *The Science and Practice of Pharmacy*, 21st Edition (2005), Part 5, "Pharmaceutical Manufacturing" [published by Lippincott Williams & Wilkins]) by bringing the described compounds of formula I or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Species like pigs, ruminants, horses, dogs, cats and poultry can be treated with the compounds according to one of embodiments 1) to 4).

Any reference to a compound according to one of embodiments 1) to 4) in this text is to be understood as referring also to the salts (and especially the pharmaceutically acceptable salts) of such compounds.

The compounds according to embodiments 1) to 4) can be used as medicaments, e.g. in the form of pharmaceutical compositions for enteral or, in particular for parenteral administration (especially intravenous application).

Another aspect of the invention concerns a method for the prevention or the treatment, preferably the treatment, of a bacterial infection in a patient, comprising the administration to said patient of a pharmaceutically active amount of a compound of formula I according to one of embodiments 1) to 4) or a pharmaceutically acceptable salt thereof. Accordingly, the invention provides a method for the prevention or the treatment of a bacterial infection mediated by Gram negative bacteria (in particular a bacterial infection mediated by *Klebsiella pneumonia* bacteria, and especially by multidrug-resistant or quinolone-resistant *Klebsiella pneumonia* bacteria and *Pseudomonas aeruginosa* bacteria) in a patient, comprising the administration to said patient of a pharmaceutically active amount of a compound of formula I according to one of embodiments 1) to 4) or a pharmaceutically acceptable salt thereof. The invention further provides a method for the prevention or the treatment, preferably the treatment, of a bacterial infection mediated by Gram positive bacteria (in particular a bacterial infection mediated by *Staphylococcus aureus* bacteria, especially by quinolone-resistant *Staphylococcus aureus* bacteria) in a patient, comprising the administration to said patient of a pharmaceutically active amount of a compound of formula I according to one of embodiments 1) to 4) or a pharmaceutically acceptable salt thereof.

The compounds of formula I according to this invention may also be used for cleaning purposes, e.g. to remove pathogenic microbes and bacteria from surgical instruments, catheters and artificial implants; to make a surface, room or an area aseptic. For such purposes, the compounds of formula I could be contained in a solution, suspension/emulssion, spray, gel and/or dry powder formulation.

The compounds according to embodiments 1) to 4) may also be used for veterinary applications, such as treating infections in livestock and companion animals. They may further constitute substances for preserving inorganic and organic materials in particular all types of organic materials for example polymers, lubricants, paints, fibres, leather, paper and wood.

The compounds according to any one of embodiments 1) to 4) are suitable for the use as active chemotherapeutic compounds in human and veterinary medicine and as substances for preserving inorganic and organic materials in particular all types of organic materials for example polymers, lubricants, paints, fibers, leather, paper and wood.

The present invention also includes isotopically labelled, especially $^2$H (deuterium) labelled compounds of formula (I), which compounds are identical to the compounds of formula (I) except that one or more atoms have each been replaced by an atom having the same atomic number but an atomic mass different from the atomic mass usually found in nature. Isotopically labelled, especially $^2$H (deuterium) labelled compounds of formula (I) and salts thereof are within the scope of the present invention. Substitution of hydrogen with the heavier isotope $^2$H (deuterium) may lead to greater metabolic stability, resulting e.g. in increased in-vivo half-life or reduced dosage requirements, or may lead to reduced inhibition of cytochrome P450 enzymes, resulting e.g. in an improved safety profile. In one embodiment of the invention, the compounds of formula (I) are not isotopically labelled, or they are labelled only with one or more deuterium atoms. In a sub-embodiment, the compounds of formula (I) are not isotopically labelled at all. Isotopically labelled compounds of formula (I) may be prepared in analogy to the methods described hereinafter, but using the appropriate isotopic variation of suitable reagents or starting materials.

The term "pharmaceutically acceptable salts" refers to salts that retain the desired biological activity of the subject compound and exhibit minimal undesired toxicological effects. Such salts include inorganic or organic acid and/or base addition salts depending on the presence of basic and/or acidic groups in the subject compound. For reference see for example 'Handbook of Pharmaceutical Salts. Properties, Selection and Use.', P. Heinrich Stahl, Camille G. Wermuth (Eds.), Wiley-VCH, 2008, and 'Pharmaceutical Salts and Co-crystals', Johan Wouters and Luc Quèrè (Eds.), RSC Publishing, 2012.

The term "prevention" is to be understood as equivalent to the term "profilaxis".

Besides, the term "room temperature" as used herein refers to a temperature of 25° C.

The compounds of formula I can be manufactured in accordance with the present invention using the procedures described hereafter.

Preparation of Compounds of Formula I

The following abbreviations are used throughout the specification and the examples:

Ac acetyl
aq. aqueous
Boc tert-butoxycarbonyl
CHO Chinese hamster ovary
CC column chromatography
DAD diode array detection
DCM dichloromethane
DME 1,2-dimethoxyethane
DMF N,N-dimethylformamide
DMAP 4-Dimethylaminopyridine
DMPK drug metabolism pharmacokinetics
DMSO-d6 deuterated dimethylsulfoxide
EA ethyl acetate
ELSD evaporative light scattering detector
ESI electron spray ionization
Et ethyl
ex. example
Hept heptane
HPLC high pressure liquid chromatography
HV high vacuum conditions
LC liquid chromatography
min minute(s)
sec seconds
Me methyl
MeCN acetonitrile
MeOH methanol
MS mass spectroscopy
NMR Nuclear Magnetic Resonance
org. organic
prep-HPLC preparative high pressure liquid chromatography
rt room temperature
sat. saturated
TBME tert-butyl methyl ether
TFA trifluoroacetic acid
THF tetrahydrofuran
TLC thin layer chromatography
$t_R$ retention time (liquid chromatography)
UV ultraviolet light All temperatures are stated in ° C. Unless otherwise indicated, the reactions take place at rt.

Analytical Methods Used

Analytical TLC characterizations were performed with 0.2 mm plates: Merck, Silica gel 60 F254. Elution is performed with EA, Hept, DCM, MeOH or mixtures thereof. Detection was done with UV or with a solution of $KMnO_4$ (10 g), $Na_2CO_3$ (20 g) and $H_2O$ (1 L) with subsequent heating.

Coloumn chromatography (CC) was performed using Brunschwig 60A silica gel (0.032-0.63 mm) or using an ISCO CombiFlash system and prepacked $SiO_2$ cartridges, elution being carried out with either Hept-EA or DCM-MeOH mixtures with an appropriate gradient.

$^1$H-NMR (400 MHz, Bruker Avance 400 or 500 MHz, Bruker Avance 500 Cryoprobe) was used to characterized the compounds. Chemical shifts δ are given in ppm relative to the solvent used; multiplicities: s=singlet, d=doublet, t=triplet, q=quadruplet, p=pentuplet, hex=hexet, hep=heptet, m=multiplet, br.=broad; coupling constants J are given in Hz.

LC-MS was used to alternatively characterized the compounds (Thermo Finnigan MSQPlus with Agilent G4220A). The analytical LC-MS data was obtained using the following respective conditions:

MS1 data:
- Column: Zorbax SB-Aq, 3.5 μm, 4.6×50 mm;
- Injection volume: 1 μL;
- Column oven temperature: 40° C.;
- Pump: Dionex HPG-3200RS;
- Makeup pump: Dionex ISO-3100SD;
- DAD: Dionex DAD-30000RS;
- MS: Thermo MSQ Plus;
- ELSD: Sedere Sedex 85;
- Detection: UV 210 nm, ELSD and MS;
- MS ionization mode: ESI+;
- Eluents: A: $H_2O$+0.04% TFA; and B: MeCN;
- Flow rate: 4.5 mL/min;
- Gradient: 5% B (0.00 min-0.01 min), 5% B to 95% B (0.01 min-1.00 min), 95% B (1.00 min-1.45 min).

MS2 data:
- Column: Zorbax RRHD SB-Aq, 3.0×50 mm, 1.8 μm;
- Injection volume: 0.30 μL;
- Column oven temperature: 40° C.;
- Pump: Agilent G4220A Binary Pump;
- Makeup pump: none;
- DAD: Agilent G4212A;
- MS: Thermo MSQ Plus;
- ELSD: Sedere Sedex 90;
- Detection: UV 210 nm, ELSD and MS;
- MS ionization mode: ESI+;
- Eluents: A: $H_2O$+0.04% TFA; and B: MeCN;
- Eluent flow rate: 0.8 mL/min;
- Gradient: 5% B to 95% B (0.0 min-1.20 min), 95% B (1.20 min-1.90 min).

MS3 data:
- Column: Waters BEH C18, 3.0×50 mm, 2.5 μm;
- Eluents: A: $H_2O/NH_3$(c($NH_3$)=13 mmol/L; and B: MeCN;
- Otherwise same parameters as for obtaining MS1 data.

The number of decimals given for the corresponding [M+H$^+$] peak(s) as well as the retention times ($t_R$) of each tested compound depends upon the accuracy of the LC-MS device actually used.

Biological Methods Used

Bacterial growth minimal inhibitory concentrations: Minimal inhibitory concentrations (MICs; mg/L) were determined in cation-adjusted Mueller-Hinton Broth by a microdilution method following the description given in "*Methods for Dilution Antimicrobial Susceptibility Tests for Bacteria that Grow Aerobically*", Approved standard, 7th ed., Clinical and Laboratory Standards Institute (CLSI) Document M7-A7, Wayne, Pa., USA (2006).

Genetic toxicology testing of compounds to assess their ability to cause DNA damage was done in vitro in mammalian cell assays (CHO cells). The formation of micronuclei, small DNA-staining particles outside of the nucleus, was investigated in mononucleated and binucleated cells treated with increasing concentrations of a test compound for 24 h. DNA was stained with Hoechst 33342 (Mutat Res. 630:1-13, 2007), read with a high-content screening microscope (Opera Phenix, Perkin Elmer) and scored with an optimized algorithm using Harmony. Micronucleii associated with valid cells were enumerated and induction of micronuclei formation tabulated as ratio versus untreated cells if the fraction of valid cells was ≥0.2.

Cytochrome P450 inhibition: The objective of this in vitro assay was to assess potential inhibition of the human cytochrome P450 (CYP450) isoforms 3A4, 2C9 and 2D6 using human liver microsomes and isoform-specific marker reactions. These data (i.e. IC50; half maximal inhibition concentration) should allow for an estimation of the potential of a compound for drug-drug interactions with co-administered drugs being metabolized via the same cytochrome P450 isoforms. This may affect plasma levels in vivo and potentially lead to adverse drug reactions or toxicity. Technically, specific marker-substrate of P450 enzymes were incubated with human liver microsomes in the presence/absence of a test compounds. The inhibition effect of the test compound towards the marker reaction was determined in incubations containing 0-100 μM of the test compound. The inhibitory effect was determined by the impact of the different compound concentrations towards the metabolite formation of the marker reaction. Formation of the metabolites was determined by LC-MS analysis.

Metabolic stability: Subcellular liver fractions and primary hepatocytes from different species were used to determine the in vitro intrinsic clearance of a compound in various species. The liver microsomal and hepatocytes in vitro half-life approach can be a suitable approach to measure intrinsic clearance in vitro, which can be scaled up to the in vivo situation and used in the prediction of human clearance (Obach et al., 1997). For this approach, liver fractions were incubated for up to 45 minutes in subcellular liver fractions or 2 h in primary hepatocytes at final compound concentration of 1 μM. Disappearance of parent compound was determined by LC-MS analysis and intrinsic clearance calculated from the slope of compound disappearance thereof.

Synthetic Preparation

EXAMPLE 1

(S)-1-{3-[(S)-2-oxo-3-(3-oxo-3,4-dihydro-2H-pyrido[3,2-b][1,4]oxazin-6-yl)-oxazolidin-5-yl]-propylamino}-1,2-dihydro-pyrrolo[3,2,1-ij]quinolin-4-one A suspension of (S)-1-amino-1,2-dihydro-pyrrolo[3,2,1-ij]quinolin-4-one (3.00 g; prepared according to WO2010/041194) and 3-[(S)-2-oxo-3-(3-oxo-3,4-dihydro-2H-pyrido[3,2-b][1,4]oxazin-6-yl)-oxazolidin-5-yl]-propionaldehyde (5.05 g; prepared according to WO2010/041194) in DCM/MeOH (5-1, 50 mL) was stirred at rt for 1 h. The mixture was cooled to 0° C., treated with NaBH(OAc)$_3$ (5.05 g; commercial) and stirred at 0° C. for 1 h. The reaction mixture was quenched by the addition of sat. $NH_4Cl$ solution. The two phases were separated and the aq. layer was extracted with DCM/MeOH (9-1). The combined org. layers were dried over $MgSO_4$. The solvents were removed under reduced pressure and the residue was purified by CC (DCM/MeOH 19:1 to 9:1) affording the title compound (4.68 g; 63% yield). MS1 (ESI, m/z): 462.02 [M+H+]; $t_R$=0.54 min. $^1$H NMR (500 MHz, DMSO-d6) δ: 11.21 (s, 1H), 7.92 (d, J=9.4 Hz, 1H), 7.55-7.60 (m, 3H), 7.43 (m, 1H), 7.21 (m, 1H), 6.57 (d, J=9.4 Hz, 1H), 4.71 (m, 2H), 4.61 (s, 2H), 4.39 (dd, J=12.8, 8.4 Hz, 1H), 4.21 (m, 1H), 4.03 (dd, J=12.8, 4.0 Hz, 1H), 3.71 (dd, J=10.0, 7.1 Hz, 1H), 2.60-2.71 (m, 2H), 1.76-1.81 (m, 2H), 1.50-1.59 (m, 2H).

EXAMPLE 2

((S)-4-oxo-1,2-dihydro-4H-pyrrolo[3,2,1-ij]quinolin-1-yl)-{3-[(S)-2-oxo-3-(3-oxo-3,4-dihydro-2H-pyrido[3,2-b][1,4]oxazin-6-ylyoxazolidin-5-yl]-propyl}-carbamic acid phosphonooxymethyl ester 2.i. ((S)-4-oxo-1,2-dihydro-4H-pyrrolo[3,2,1-ij]quinolin-1-yl)-{3-[(S)-2-oxo-3-(3-oxo-3,4-dihydro-2H-pyrido[3,2-b][1,4]oxazin-6-yl)-oxazolidin-5-yl]-propyl}-carbamic acid chloromethyl ester To a suspension of the compound of example 1 (9 g) in DCM (80 mL) were added N,N,N',N'-tetramethyl-1,8-naphthalenediamine (8.44 g; commercial) and chloromethyl chloroformate (1.91 mL, prepared according to US2004/0152911) and the mixture was stirred at rt for 90 min. 10% citric acid was added, the phases were separated and the aq. layer was extracted with DCM. The combined org. layers were washed with water and brine and dried over MgSO$_4$. The solvents were removed under reduced pressure and the residue was purified by CC (DCM/MeOH 19:1) affording the title compound as a colorless solid (10.09 g; 93% yield). MS1 (ESI, m/z): 553.95 [M+H$^+$]; t$_R$=0.79 min.

2.ii. 6-((S)-5-{3-[chloromethoxycarbonyl-((S)-4-oxo-1,2-dihydro-4H-pyrrolo[3,2,1-ij]quinolin-1-yl)-amino]-propyl}-2-oxo-oxazolidin-3-yl)-3-oxo-2,3-dihydro-pyrido[3,2-b][1,4]oxazine-4-carboxylic acid tert-butyl ester A solution of intermediate 2.i (4.55 g) in DCM (32 mL) was treated with Boc$_2$O (1.88 g) and DMAP (50 mg) and the mixture was stirred at rt for 90 min. The solution was diluted with DCM and water was added, the phases were separated and the aq. layer was extracted with DCM. The combined org. layers were washed with water and brine and dried over MgSO$_4$. The solvents were removed under reduced pressure and the residue was purified by CC (DCM/MeOH 1:0 to 9:1) affording the title compound as a colorless solid (4.1 g; 76% yield). MS2 (ESI, m/z): 653.91 [M+H$^+$]; t$_R$=1.04 min.

2. iii. 6-((S)-5-{3-[(di-tert-butoxy-phosphoryloxymethoxycarbonyl)-((S)-4-oxo-1,2-dihydro-4H-pyrrolo[3,2,1-ij]quinolin-1-yl)-amino]-propyl}-2-oxo-oxazolidin-3-yl)-3-oxo-2,3-di hydro-pyrido[3,2-b][1,4]oxazine-4-carboxylic acid tert-butyl ester A solution of intermediate 2.ii (5.0 g) in DME (76 mL) and tetrabutylammonium di-tert-butylphosphate (4.1 g; commercial) was heated at 55° C. for 2 h. After cooling to rt EA and water were added and the phases were separated. The aq. layer was extracted with EA and the combined org. layers were washed with water, sat. NaHCO$_3$ and brine and dried over MgSO$_4$. The solvents were removed under reduced pressure and the residue was purified by CC (EA/MeOH 1:0 to 9:1) affording the title compound as a colorless solid (4.7 g; 74% yield). MS2 (ESI, m/z): 828.42 [M+H$^+$]; t$_R$=1.09 min.

2.iv. ((S)-4-oxo-1,2-dihydro-4H-pyrrolo[3,2,1-ij]quinolin-1-yl)-{3-[(S)-2-oxo-3-(3-oxo-3,4-dihydro-2H-pyrido[3,2-b][1,4]oxazin-6-yl)-oxazolidin-5-yl]-propyl}-carbamic acid phosphonooxymethyl ester A solution of intermediate 2.iii (414 mg) in DCM (5 mL) was cooled to 0° C. and treated with TFA (0.77 mL). The mixture was stirred at 0° C. for 2 h. TBME (5 mL) was added and the resulting suspension was stirred at 0° C. for 15 min, filtered and dried at HV. The obtained solid was dissolved in MeCN/water (1:1, 12 mL) and lyophilized to afford the title compound as colourless lyophilisate (276 mg; 90% yield).

$^1$H NMR (DMSO-d6) δ: 11.22 (s, 1H), 7.93 (d, J=9.4 Hz, 1H), 7.66-7.40 (m, 4H), 7.20 (m, 1H), 6.60 (d, J=9.4 Hz, 1H), 6.15-5.37 (m, 2H), 4.67-4.45 (m, 4H), 4.25-4.05 (m, 2H), 3.74-2.92 (m, 4H), 1.75-1.41 (m, 4H). MS3 (ESI, m/z): 615.92 [M+H$^+$]; t$_R$=0.42 min.

EXAMPLE 3

3-(2-phosphonooxy-phenyl)-propionic acid (((S)-4-oxo-1,2-dihydro-4H-pyrrolo[3,2,1-ij]quinolin-1-yl)-{3-[(S)-2-oxo-3-(3-oxo-3,4-dihydro-2H-pyrido[3,2-b][1,4]oxazin-6-yl)-oxazolidin-5-yl]-propyl}-carbamoyloxyymethyl ester

3.i. 3-[2-(di-tert-butoxy-phosphoryloxy)-phenyl] propionic acid methyl ester To a solution of methyl 3-(2-hydroxyphenyl)propionate (7.5 g; commercial) in THF (250 mL) at 0° C. were added tetrazole (0.45 M in MeCN, 138 mL; commercial) and di-tert-butyl N,N-diisopropylphosphoramidite (17.3 mL, commercial) and the solution was stirred at rt for 2 h. Additional di-tert-butyl N,N-diisopropylphosphoramidite (6.63 mL, commercial) and tetrazole (0.45 M in MeCN, 18.5 mL; commercial) were added and the resulting mixture was stirred at rt for 3.5 h. The mixture was cooled to 0° C. and 30% aq. H$_2$O$_2$ (41 mL) was added drop wise. The mixture was stirred at 0° C. for 0.75 h. Water was added to the mixture and the aq. layer was extracted with EA. The combined org. layers were washed with water and brine and dried over MgSO$_4$. The solvents were removed under reduced pressure and the residue was purified by CC (Hept/EA 99:1 to 0:1) affording the title compound as a yellow liquid (9.05 g; 58% yield). MS1 (ESI, m/z): 372.96 [M+H$^+$]; t$_R$=0.91 min. $^1$H NMR (500 MHz, CDCl$_3$) δ: 1.53 (s, 18H), 2.67 (m, 2H), 3.03 (m, 2H), 3.69 (s, 3H), 7.08 (t, J=7.5 Hz, 1H), 7.20 (m, 2H), 7.42 (d, J=8.2 Hz, 1H).

3-[2-(di-tert-butoxy-phosphoryloxy)-phenyl]propionic acid

To a solution of intermediate 3.i (9 g) in a mixture of THF (100 mL), MeOH (100 mL) and water (50 mL) was added lithium hydroxide monohydrate (4.1 g; commercial) and the mixture was stirred at rt for 1.5 h. The majority of the solvent was evaporated and the residual aq. layer was extracted with TBME. The aq. layer was acidified with 10% citric acid to reach pH 3 and was then extracted with EA. The combined org. layers were washed with water and brine and dried over MgSO$_4$. The solvents were removed under reduced pressure affording the title compound as an unstable yellow solid (7.95 g; 92% yield) which was directly used in the next step. MS1 (ESI, m/z): 359.22 [M+H$^+$]; t$_R$=0.81 min. $^1$H NMR (500 MHz, CDCl$_3$) δ: 1.53 (s, 18H), 2.71 (m, 2H), 3.05 (m, 2H), 7.11 (t, J=7.4 Hz, 1H), 7.22 (m, 2H), 7.35 (d, J=8.2 Hz, 1H).

3.iii 3-[2-(di-tert-butoxy-phosphoryloxy)-phenyl]-propionic acid (((S)-4-oxo-1,2-dihydro-4H-pyrrolo[3,2,1-ij]quinolin-1-yl)-{3-[(S)-2-oxo-3-(3-oxo-3,4-dihydro-2H-pyrido[3,2-b][1,4]oxazin-6-yl)-oxazolidin-5-yl]-propyl}-carbamoyloxy)-methyl ester To a solution of intermediate 2.i (2.49 g) in DMF (27 mL) were added intermediate 3.ii (1.77 g) and K$_2$CO$_3$ (1.37 g) and the resulting suspension was stirred at 40° C. for 2 h. After cooling to rt, EA and sat. NaHCO$_3$ were added and the phases were separated. The aq. layer was extracted with EA and the combined organic layers were washed with water and brine and dried over $MgSO_4$. The solvents were removed under reduced pressure and the residue was purified by CC (DCM/MeOH 1:0 to 19:1) affording the title compound as a colorless solid (2.17 g; 55% yield). MS1 (ESI, m/z): 876.54 [M+H$^+$]; $t_R$=0.94 min.

3.iv. 3-(2-Phosphonooxy-phenyl)-propionic acid (((S)-4-oxo-1,2-dihydro-4H-pyrrolo[3,2,1-ij]quinolin-1-yl)-{3-[(S)-2-oxo-3-(3-oxo-3,4-dihydro-2H-pyrido[3,2-b][1,4]oxazin-6-yl)-oxazolidin-5-yl]-propyl}-carbamoyloxy)-methyl ester To a solution of intermediate 3.iii (2.16 g) in DCM (25 mL) was added TFA (2.83 mL) at 0° C. and the solution was stirred at 0° C. for 3 h. TBME (25 mL) was added at 0° C. and the resulting suspension was stirred at that temperature for 10 min and was then filtered. The resulting colorless solid was then suspended in water (100 mL). Under vigorous stirring sat. $NaHCO_3$ was slowly added until the solid was dissolved (pH 8). The aq. solution was extracted with EA to remove organic side products. The aq. layers were cooled to 0° C. and then acidified with HCl 1M to reach pH 1. The resulting suspension was filtered and the solid was dried at HV. The obtained solid was dissolved in MeCN/water (1:1, 60 mL) and lyophilized to afford the title compound as colourless lyophilisate (1.58 g; 84% yield). MS1 (ESI, m/z): 764.18 [M+H$^+$]; $t_R$=0.67 min. $^1$H NMR (DMSO-d6) δ: 7.90 (d, J=9.4 Hz, 1H), 7.59 (d, J=8.7 Hz, 2H), 7.38 (m, 3H), 7.16-7.22 (m, 3H), 7.04 (t, J=7.4 Hz, 1H), 6.95-6.20 (m, 3H), 5.79-5.50 (m, 3H), 4.55-4.63 (m, 4H), 4.21 (m, 2H), 3.68 (m, 1H), 3.45-3.20 (m, 2H), 2.89 (m, 2H), 2.60 (m, 2H), 1.67 (s, 2H), 1.40-1.30 (m, 2H).

Pharmacological Properties

The compound of Example 1 according to the present invention (inv.) and reference compounds 4 (ref.) to 9 (ref.) were tested against several Gram-positive and Gram-negative bacteria. *Staphylococcus aureus* A798 is a multiply resistant strain (in particular quinolone-resistant), *Klebsiella pneumoniae* A-651 is a multiply resistant strain (in particular quinolone-resistant), while *E. coli* ATCC25922 and *P. aeruginosa* ATCC27853 are quinolone-sensitive strains. The corresponding antibacterial test results are given in Table 1 hereafter (MICs in mg/L).

TABLE 1

| Example No. | Reference Example, as published | MIC for S. aureus A798 | MIC for E. coli ATCC25922 | MIC for K. Pneumoniae A-651 | MIC for P. aeruginosa AT0027853 |
|---|---|---|---|---|---|
| 1 (inv.) | — | 0.031 | 0.25 | 0.5 | 1 |
| 4 (ref.) | ex. 189, WO2010/041194 | ≤0.031 | 0.25 | 0.5 | 1 |
| 5 (ref.) | ex. 74, WO2010/041194 | 0.031 | 0.25 | 0.5 | 2 |
| 6 (ref.) | ex. 135, WO2010/041194 | 0.063 | 0.25 | 1 | 2 |
| 7 (ref.) | ex. 86, WO2010/041194 | 0.063 | 0.5 | 2 | 2 |
| 8 (ref.) | ex. 136, WO2010/041194 | ≤0.031 | 0.125 | 0.25 | 1 |
| 9 (ref.) | ex. 33, WO2014/108832 | 0.063 | 1 | 2 | 8 |

The compounds of Examples 2 and 3 of the present invention (inv.) were tested against wild-type *E. coli* A-1261 in the presence of alkaline phosphatase (from bovine intestinal mucosa: Sigma P6774-2KU; Lot: SLBB1168) or esterase (from porcine liver: Sigma E2884-5KU; Lot: 129K7010V), and in the absence of an alkaline phosphatase and esterase. The corresponding antibacterial test results are given in Table 2 hereafter (MICs in mg/L).

TABLE 2

| | | MIC for *E. coli* A-1261 | | |
|---|---|---|---|---|
| Example No. | Active metabolite Example No. | In the absence of alkaline phosphatase and esterase | In the presence of an alkaline phosphatase (2 i.U./mL) | In the presence of an esterase (10 i.U./mL) |
| 2 (inv.) | 1 (inv.) | >8 | 0.25 | >8 |
| 3 (inv.) | 1 (inv.) | >8 | 0.25 | 1 |

Genetic toxicity potential of the compound of Example 1 according to the present invention (inv.) and reference compounds (ref.) was assessed and the corresponding test results are given in Table 3 hereafter.

TABLE 3

| Example No. | Reference Example, as published | Maximal induction of micronuclei formation normalized vs. background |
|---|---|---|
| 1 (inv.) | — | 2.5 |
| 4 (ref.) | ex. 189, WO2010/041194 | 7.0 |
| 5 (ref.) | ex. 74, WO2010/041194 | 3.8 |
| 6 (ref.) | ex. 135, WO2010/041194 | 3.1 |
| 7 (ref.) | ex. 86, WO2010/041194 | 2.9 |
| 8 (ref.) | ex. 136, WO2010/041194 | 4.1 |

Metabolic stability of the compounds according to the present invention (inv.) and reference compounds (ref.) in human liver microsomes and inhibition of the human cytochrome P450 (CYP450) isoforms 3A4, 2C9 and 2D6 are given in Table 4 hereafter.

TABLE 4

| Example No. | Reference Example, as Published | CYP450 lowest IC50 of the isoenzymes measured (μM) | Intrinsic clearance in human liver microsomes (μL/min * mg microsomal protein) |
|---|---|---|---|
| 1 (inv.) | — | >50 | 15 |
| 4 (ref.) | ex. 189, WO2010/041194 | >50 | 21 |
| 5 (ref.) | ex. 74, WO2010/041194 | 23 | 35 |
| 6 (ref.) | ex. 135, WO2010/041194 | 29 | 28 |
| 7 (ref.) | ex. 86, WO2010/041194 | 28 | 38 |
| 8 (ref.) | ex. 136, WO2010/041194 | 22 | 115 |

Surprisingly, the compound of Example 1 according to the present invention not only shows excellent antimicrobial activity against several bacterial strains (Table 1), it also exhibits superior pharmacological properties (Tables 3 and 4). The compounds according to Examples 2 and 3 exhibit antimicrobial activity in biologically relevant environment via formation of the compound of Example 1 (Table 2).

The invention claimed is:

1. A compound of formula I

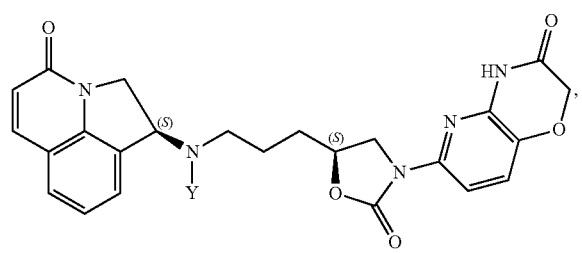

I wherein Y represents hydrogen or a group selected from $Y^1$ or $Y^2$

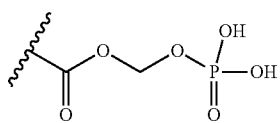

$Y^1$

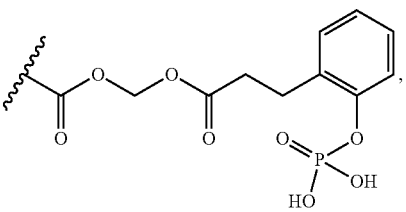

$Y^2$ or a salt thereof.

2. The compound according to claim 1 which is (S)-1-{3-[(S)-2-oxo-3-(3-oxo-3,4-dihydro-2H-pyrido[3,2-b][1,4]oxazin-6-yl)-oxazolidin-5-yl]-propylamino}-1,2-dihydro-pyrrolo[3,2,1-ij]quinolin-4-one or a pharmaceutically acceptable salt thereof.

3. The compound according to claim 1 which is ((S)-4-oxo-1,2-dihydro-4H-pyrrolo[3,2,1-ij]quinolin-1-yl)-{3-[(S)-2-oxo-3-(3-oxo-3,4-dihydro-2H-pyrido[3,2-b][1,4]oxazin-6-yl)-oxazolidin-5-yl]-propyl}-carbamic acid phosphonooxymethyl ester or a pharmaceutically acceptable salt thereof.

4. The compound according to claim 1 which is 3-(2-phosphonooxy-phenyl)-propionic acid(((S)-4-oxo-1,2-dihydro-4H-pyrrolo[3,2,1-ij]quinolin-1-yl)-{3-[(S)-2-oxo-3-(3-oxo-3,4-dihydro-2H-pyrido[3,2-b][1,4]oxazin-6-yl)-oxazolidin-5-yl]-propyl}-carbamoyloxy)-methyl ester or a pharmaceutically acceptable salt thereof.

5. A composition comprising the compound of claim 1, or a pharmaceutically acceptable salt thereof, further comprising at least one pharmaceutically acceptable excipient.

6. A medicament comprising the compound of claim 1, or a pharmaceutically acceptable salt thereof.

7. A method for treatment of a bacterial infection comprising administering the compound of claim 1, or a pharmaceutically acceptable salt thereof.

8. A method for treatment of a bacterial infection mediated by Gram-negative bacteria comprising administering the compound of claim 1, or a pharmaceutically acceptable salt thereof.

9. A method for treatment of a bacterial infection mediated by bacteria selected from the group comprising *Staphylococcus aureus*, *Klebsiella pneumoniae*, *Escherichia coli* and *Pseudomonas aeruginosa* comprising administering the compound of claim 1, or a pharmaceutically acceptable salt thereof.

* * * * *